(12) United States Patent
Lagrange et al.

(10) Patent No.: US 7,481,847 B2
(45) Date of Patent: Jan. 27, 2009

(54) DYE COMPOSITION COMPRISING AT LEAST ONE CATIONIC HYDRAZONE DIRECT DYE, DYEING PROCESS, AND MULTI-COMPARTMENT DEVICES

(75) Inventors: Alain Lagrange, Coupvray (FR); Leïla Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 70 days.

(21) Appl. No.: 11/727,532

(22) Filed: Mar. 27, 2007

(65) Prior Publication Data

US 2007/0234487 A1 Oct. 11, 2007

Related U.S. Application Data

(60) Provisional application No. 60/792,956, filed on Apr. 19, 2006.

(30) Foreign Application Priority Data

Mar. 28, 2006 (FR) .................................. 06 51074

(51) Int. Cl.
*A61Q 5/10* (2006.01)
*C07D 239/00* (2006.01)
*C07C 50/18* (2006.01)

(52) U.S. Cl. ....................... 8/405; 8/406; 8/423; 8/426; 8/435; 8/565; 8/567; 8/643; 552/208; 544/242

(58) Field of Classification Search ............... 8/405, 8/406, 423, 426, 435, 565, 567, 643; 552/208; 544/242

See application file for complete search history.

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 2,798,053 A | 7/1957 | Brown |
| 2,923,692 A | 2/1960 | Ackerman et al. |
| 3,812,107 A * | 5/1974 | Boehmke et al. ............ 544/316 |
| 3,840,518 A | 10/1974 | Schmitt et al. |
| 3,860,583 A | 1/1975 | Schmitt |
| 3,915,921 A | 10/1975 | Schlatzer, Jr. |
| 4,003,699 A | 1/1977 | Rose et al. |
| RE30,199 E | 1/1980 | Rose et al. |
| 4,237,243 A | 12/1980 | Quack et al. |
| 4,509,949 A | 4/1985 | Huang et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,733,343 A | 3/1998 | Möckli |
| 5,766,576 A | 6/1998 | Lowe et al. |
| 5,888,252 A | 3/1999 | Möckli |
| 6,099,592 A | 8/2000 | Vidal et al. |
| 6,099,593 A | 8/2000 | Terranova et al. |
| 6,284,003 B1 | 9/2001 | Rose et al. |
| 6,645,258 B2 | 11/2003 | Vidal et al. |
| 6,824,570 B2 | 11/2004 | Vidal et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,077,873 B2 | 7/2006 | David et al. |
| 7,261,743 B2 | 8/2007 | Plos et al. |
| 7,300,473 B2 | 11/2007 | Lang et al. |
| 7,407,516 B2 | 8/2008 | Vidal |
| 2002/0095732 A1 | 7/2002 | Kravtchenko et al. |
| 2005/0144741 A1 | 7/2005 | Lang et al. |
| 2005/0235433 A1 | 10/2005 | Rondeau |
| 2006/0117497 A1 | 6/2006 | Lang et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 216 479 | 4/1987 |
| EP | 0 714 954 | 6/1996 |
| EP | 0 770 375 | 5/1997 |
| EP | 0 970 684 | 1/2000 |
| EP | 0 970 685 | 1/2000 |
| EP | 0 970 687 | 1/2000 |
| FR | 2 416 723 | 9/1979 |
| FR | 2 586 913 | 3/1987 |
| FR | 2 733 749 | 11/1996 |
| FR | 2 750 048 | 12/1997 |
| FR | 2 807 650 | 10/2001 |
| FR | 2 822 693 | 10/2002 |
| FR | 2 822 694 | 10/2002 |
| FR | 2 822 696 | 10/2002 |

(Continued)

OTHER PUBLICATIONS

STIC Search Report dated Jul. 17, 2008.*

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

The present disclosure relates to a composition for dyeing human keratin fibers, comprising at least one cationic direct dye of formula (I), described herein, and at least one cosmetic agent chosen from thickening agents and surfactants. Also disclosed herein is a dyeing process comprising applying a composition of the present disclosure to keratin fibers, in the presence or absence of an oxidizing agent. Further disclosed herein is a multi-compartment device comprising at least one first compartment containing a dye composition of the present disclosure and at least one second compartment containing at least one oxidizing composition.

25 Claims, No Drawings

FOREIGN PATENT DOCUMENTS

| | | |
|---|---|---|
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 769163 | 2/1957 |
| GB | 1026978 | 4/1966 |
| GB | 1153196 | 5/1969 |
| JP | 2-019576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078660 | 10/2002 |
| WO | WO 02/100369 | 12/2002 |
| WO | WO 02/100834 | 12/2002 |

OTHER PUBLICATIONS

English language esp@cenet abstract for EP 0 770 375 (1997).
English language esp@cenet abstract for EP 0 970 685 (2000).
English language esp@cenet abstract for JP 2-019576 (1990).
English language esp@cenet abstract for JP 5-163124 (1993).
International Search Report for FR 06 51074, Dec. 19, 2006, corresponding to the present application.
International Search Report for EP 07 10 4860, Jun. 25, 2007, corresponding to the present application.
International Cosmetic Ingredient Dictionary, Fifth Ed. (1993).
Kirk-Othmer, "Encyclopedia of Chemical Technology," Third Ed., vol. 3, pp. 896-900 (1978).
MacGregor and Greenwood., "Polymers in Nature," John Wiley & Sons, Chapter 6, pp. 240-328 (1980).
Porter, "Handbook of Surfactants," Blackie & Son, Glasgow and London, pp. 116-178 (1991).
Whistler, "Industrial Gums - Polysaccharides and their Derivatives," 2d ed., Academic Press, New York and London (1973).

* cited by examiner

DYE COMPOSITION COMPRISING AT LEAST ONE CATIONIC HYDRAZONE DIRECT DYE, DYEING PROCESS, AND MULTI-COMPARTMENT DEVICES

CROSS-REFERENCE TO RELATED APPLICATIONS

This application claims benefit of U.S. Provisional Application No. 60/792,956, filed Apr. 19, 2006, the contents of which are incorporated herein by reference. This application also claims benefit of priority under 35 U.S.C. § 119 to French Patent Application No. FR 06 51074, filed Mar. 28, 2006, the contents of which are also incorporated herein by reference.

FIELD OF THE INVENTION

Disclosed herein is a dye composition for dyeing human keratin fibers such as the hair, comprising at least one cationic hydrazone direct dye. Also disclosed herein are processes for dyeing human keratin fibers comprising applying such a composition to the hair. Further disclosed herein is a device for implementing the processes of the present disclosure.

BACKGROUND OF THE INVENTION

It is known practice to dye human keratin fibers, such as the hair, with dye compositions comprising oxidation dye precursors, which are generally known as oxidation bases and couplers. These oxidation bases and couplers are colorless or weakly colored compounds, which, when combined with oxidizing agents such as peroxides, for example, hydrogen peroxide, give rise to colored compounds by a process of oxidative condensation.

The colorations resulting therefrom are permanent, strong, and resistant to external agents, such as light, bad weather, washing, perspiration, and/or rubbing. This process, which is generally applied at basic pH, makes it possible simultaneously to dye and lighten the fibers, which is reflected in practice by the possibility of obtaining a final coloration that is lighter than the original color. In addition, lightening of the fiber may have the advantageous effect of generating a unified color in the case of grey hair, and of bringing out the color, i.e., making it more visible, in the case of naturally pigmented hair.

It is also known practice to dye human keratin fibers with a direct dye. The process conventionally used in direct dyeing comprises applying direct dyes to the keratin fibers, which are colored and coloring molecules that have affinity for the fibers, leaving the dyes on the fibers, and then rinsing the fibers.

It is known practice, for example, to use direct dyes chosen from nitrobenzene, anthraquinone, nitropyridine, azo, xanthene, acridine, azine, and triarylmethane direct dyes.

The colorations resulting therefrom are particularly chromatic colorations, but are, however, temporary or semi-permanent since the nature of the interactions linking the direct dyes to the keratin fiber, and their desorption from the surface and/or core of the fiber are generally considered responsible for their poor dyeing power and their poor fastness with respect to washing and/or perspiration. These direct dyes are also generally light-sensitive due to the poor resistance of the chromophore with respect to photochemical attack, and often lead, over time, to fading of the coloration of the hair. In addition, their light-sensitivity is dependent on their uniform distribution or their distribution as aggregates in the keratin fiber.

The direct dyes may be combined with oxidizing agents. However, the direct dyes are often sensitive to the action of oxidizing agents and reducing agents, which makes them generally difficult to use in lightening direct dyeing compositions based on aqueous hydrogen peroxide solution and based on a basifying agent, or in oxidation dye compositions in combination with precursors such as oxidation bases or couplers.

SUMMARY OF THE INVENTION

It would thus be desirable to provide chromatic direct dyes that allow human keratin fibers to be dyed as strongly as with oxidation dyes, which may be just as light-fast as the latter dyes, and which may also be resistant to bad weather, washing, and/or perspiration, and may also be sufficiently stable in the presence of oxidizing and reducing agents to be able simultaneously to obtain lightening of the fiber either by using lightening direct compositions containing them, or by using oxidation dye compositions based on oxidation dye precursors containing them.

It would also be desirable to provide direct dyes that can produce color uptakes comparable to those obtained with oxidation dye precursors.

In addition, it would also be desirable to further improve the harmlessness of dyes, and to search for dyes that do not degrade keratin fibers, and that have reduced selectivity as compared with standard dyes.

DETAILED DESCRIPTION OF THE INVENTION

The compositions, methods, and devices of the present disclosure achieve at least one of the above-mentioned benefits. Thus, at least one embodiment of the present disclosure relates to a dye composition comprising, in a medium that is suitable for dyeing human keratin fibers:

(a) at least one cationic direct hydrazone dye chosen from compounds of formula (I), and tautomeric forms thereof:

$$[A\text{-}C(R_3)\!=\!N\!-\!N(R_1)\!-\!B]^+ X \qquad (I)$$

wherein:

$R_1$ and $R_3$, which may be identical or different, are chosen from hydrogen and linear or branched $C_1$-$C_{10}$ alkyl radicals optionally bearing a hydroxyl group, and in at least one embodiment, from hydrogen and linear or branched $C_1$-$C_{10}$ alkyl radicals;

A is a fused or non-fused, optionally substituted cationic heterocycle chosen from pyrimidinone, indole, and benzothiazole rings; the ring A being linked to the carbon of $C(R_3)$ via a carbon atom;

B is a saturated or unsaturated, optionally substituted tricycle chosen from dibenzofurans, carbazoles, anthraquinones, and dibenzothienyls; the saturated or unsaturated tricycle being linked to the nitrogen atom of the hydrazone function via a carbon atom of one of the three rings; and X is chosen from anions and mixtures of anions that are cosmetically acceptable; and (b) at least one cosmetic agent chosen from thickening polymers and surfactants.

Also disclosed herein is a process for dyeing human keratin fibers, such as the hair, comprising applying the composition described above to the fibers and leaving it to act for a time that is sufficient to obtain the desired coloration.

Further disclosed herein is a multi-compartment device comprising at least one first compartment containing a dye composition comprising a dye of formula (I) and at least a second compartment containing at least one oxidizing composition.

Still further disclosed herein is the use of a dye of formula (I) for dyeing keratin fibers.

Other advantages and characteristics of the present disclosure will emerge more clearly upon reading the description and the examples that follow.

In the text hereinbelow and unless otherwise indicated, the limits delimiting a range of values are included in that range of values.

Direct Dyes

According to one embodiment of the present disclosure, the composition comprises a compound of formula (I) wherein one of the tautomeric forms of this dye (I) has a quaternized nitrogen atom engaged in the heterocycle.

For example, this quaternized nitrogen atom may bear at least one substituent chosen from linear or branched $C_1$-$C_{10}$, for instance $C_1$-$C_6$, alkyl radicals; linear or branched $C_1$-$C_{10}$, for example $C_1$-$C_6$, hydroxyalkyl radicals; benzyl radicals, and phenyl radicals, the aromatic nucleus of the benzyl and phenyl groups possibly being substituted with at least one radical chosen from $C_1$-$C_4$ alkyl, $C_1$-$C_4$ alkoxy, $C_1$-$C_4$ hydroxyalkyl, amino, and halogen radicals. In at least one embodiment, the at least one substituent may be chosen from linear or branched $C_1$-$C_4$ alkyl and hydroxyalkyl radicals.

The heterocycle or the heterocyclic portion of the group A may be optionally substituted with at least one radical chosen from linear or branched $C_1$-$C_6$ alkyl radicals, such as methyl and ethyl; hydroxyl radicals, amino radicals, $C_1$-$C_4$ alkoxy radicals, and halogen radicals. In at least one embodiment, the at least one radical is chosen from linear or branched $C_1$-$C_4$ alkyl radicals.

The aromatic portion of the group A is optionally substituted with at least one radical chosen from trifluoromethyl; ($C_1$-$C_6$)alkoxycarbonyl; nitro, hydroxyl, $C_1$-$C_4$ alkyl, $C_1$-$C_4$ alkoxy, amino, and halogen radicals.

The group B may be optionally substituted with at least one radical chosen from linear or branched $C_1$-$C_6$ alkyl radicals; linear or branched $C_1$-$C_6$ alkoxy radicals; amino radicals; amino radicals substituted with one or two linear or branched $C_1$-$C_6$ alkyl radicals, which may be identical or different; phenylamino radicals for which the phenyl group may be substituted with at least one radical chosen from $C_1$-$C_6$ alkyl, $C_1$-$C_6$ alkoxy, and halogen radicals, amine radicals optionally substituted with at least one $C_1$-$C_6$ alkyl group, which may be identical or different; hydroxyl groups; halogen atoms; and nitro groups.

When B is an anthraquinone group attached via one of the carbon atoms of one of the aromatic nuclei to the nitrogen atom of the hydrazone function, it may then be substituted, in at least one embodiment on the other aromatic nucleus, with a group of formula A-C($R_3$)=N—N($R_1$)—, wherein A, $R_3$, and $R_1$ have the same meanings defined above and are chosen such that they are, respectively, identical to those of the other portion of the molecule of formula (I).

According to one embodiment of the present disclosure, in the case of a group B of anthraquinone type, the radical $R_1$ is a hydrogen atom.

According to another embodiment of the present disclosure, when the group A is an indole and the group B is a carbazole group, then the group A is substituted on the aromatic portion of the group, as described above.

Examples of anions and mixtures of anions, X, that are cosmetically acceptable include, but are not limited to, halides such as chlorides, bromides, fluorides, and iodides; hydroxides; sulfates; hydrogen sulfates; ($C_1$-$C_6$)alkyl sulfates; phosphates; carbonates; hydrogen carbonates; perchlorates; acetates; tartrates; citrates; oxalates; ($C_1$-$C_6$)-alkylsulfonates such as methylsulfonate; arylsulfonates that are optionally substituted with a $C_1$-$C_4$ alkyl radical, for instance, 4-tolylsulfonate; and trichlorozincates.

The dyes of the present disclosure may be chosen from compounds that are known in the art. Non-limiting examples of these dyes and the tautomeric forms thereof include:

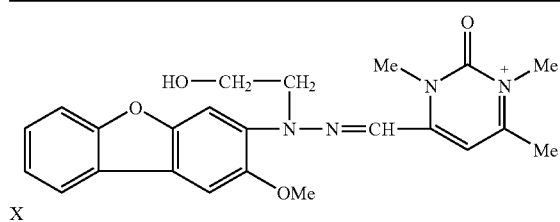

Pyrimidinium salt, 2,3-dihydro-4-[[(2-hydroxyethyl)(2-methoxy-3-dibenzofuranyl)hydrazono]methyl]-1,3,6-trimethyl-2-oxo

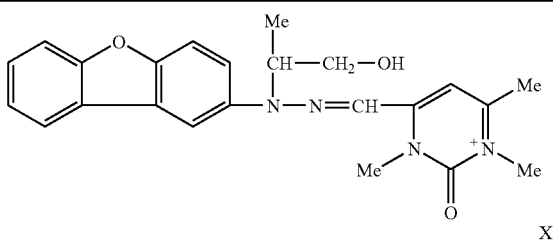

Pyrimidinium salt, 4-[[2-dibenzofuranyl(2-hydroxy-1-ethylethyl)hydrazono]methyl]-2,3-dihydro-1,3,6-trimethyl-2-oxo-

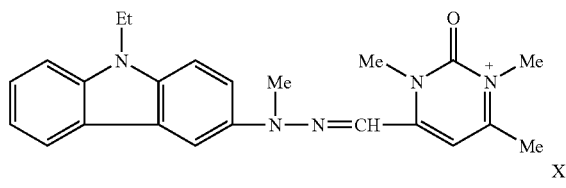

Pyrimidinium salt, 4-[[(9-ethyl-9H-carbazol-3-yl)methylhydrazono]methyl]-2,3-dihydro-1,3,6-trimethyl-2-oxo-(9Cl)

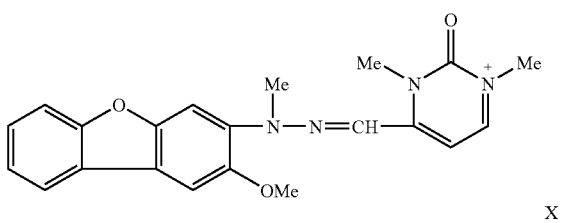

Pyrimidinium salt, 2,3-dihydro-4-[[(2-methoxy-3-dibenzofuranyl)methylhydrazono] methyl]-1,3-dimethyl-2-oxo-(9Cl)

-continued

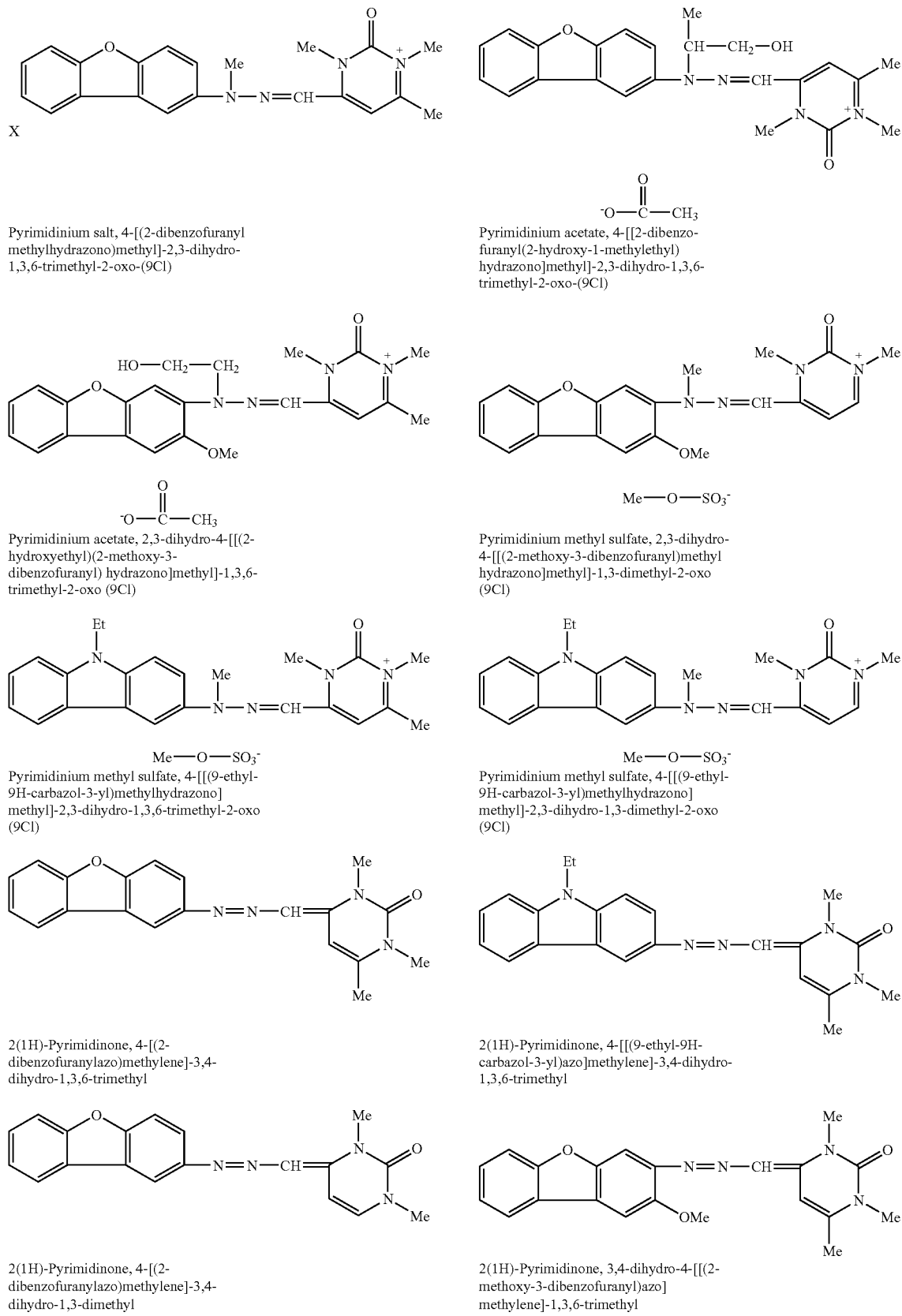

Pyrimidinium salt, 4-[(2-dibenzofuranyl methylhydrazono)methyl]-2,3-dihydro-1,3,6-trimethyl-2-oxo-(9CI)

Pyrimidinium acetate, 4-[[2-dibenzo-furanyl(2-hydroxy-1-methylethyl) hydrazono]methyl]-2,3-dihydro-1,3,6-trimethyl-2-oxo-(9CI)

Pyrimidinium acetate, 2,3-dihydro-4-[[(2-hydroxyethyl)(2-methoxy-3-dibenzofuranyl) hydrazono]methyl]-1,3,6-trimethyl-2-oxo (9CI)

Pyrimidinium methyl sulfate, 2,3-dihydro-4-[[(2-methoxy-3-dibenzofuranyl)methyl hydrazono]methyl]-1,3-dimethyl-2-oxo (9CI)

Pyrimidinium methyl sulfate, 4-[[(9-ethyl-9H-carbazol-3-yl)methylhydrazono] methyl]-2,3-dihydro-1,3,6-trimethyl-2-oxo (9CI)

Pyrimidinium methyl sulfate, 4-[[(9-ethyl-9H-carbazol-3-yl)methylhydrazono] methyl]-2,3-dihydro-1,3-dimethyl-2-oxo (9CI)

2(1H)-Pyrimidinone, 4-[(2-dibenzofuranylazo)methylene]-3,4-dihydro-1,3,6-trimethyl 2(1H)-Pyrimidinone, 4-[[(9-ethyl-9H-carbazol-3-yl)azo]methylene]-3,4-dihydro-1,3,6-trimethyl 2(1H)-Pyrimidinone, 4-[(2-dibenzofuranylazo)methylene]-3,4-dihydro-1,3-dimethyl 2(1H)-Pyrimidinone, 3,4-dihydro-4-[[(2-methoxy-3-dibenzofuranyl)azo] methylene]-1,3,6-trimethyl -continued

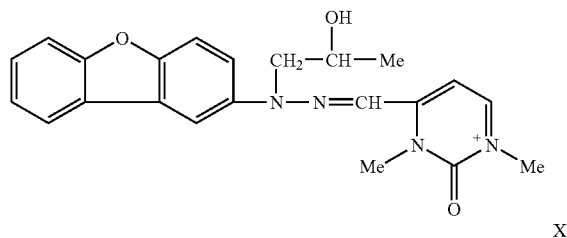

Pyrimidinium salt, 4-[[2-dibenzofuranyl
(2-hydroxypropyl)hydrazono]methyl]-2,3-
dihydro-1,3-dimethyl-2-oxo-

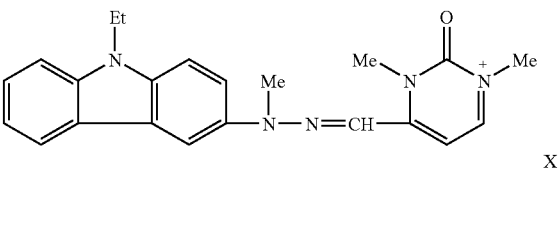

Pyrimidinium salt, 4-[[(9-ethyl-9H-
carbazol-3-yl)methylhydrazono]methyl]-
2,3-dihydro-1,3-dimethyl-2-oxo (9Cl)

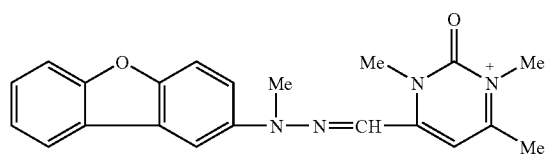

Pyrimidinium methyl sulfate, 4-[(2-
dibenzofuranylmethylhydrazono)methyl]-
2,3-dihydro-1,3,6-trimethyl-2-oxo (9Cl)

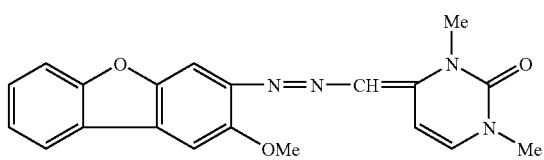

2(1H)-Pyrimidinone, 3,4-dihydro-4-[[(2-
methoxy-3-dibenzofuranyl)azo]
methylene]-1,3-dimethyl

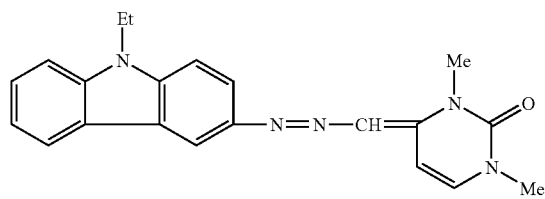

2(1H)-Pyrimidinone, 4-[[(9-ethyl-9H-
carbazol-3-yl)azo]methylene]-3,4-
dihydro-1,3-dimethyl

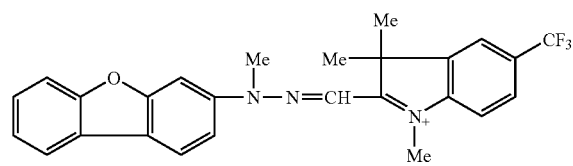

3H-Indolium methyl sulfate, 2-[(2-
dibenzofuranylmethylhydrazono)methyl]-
5-trifluoromethyl)-1,3,3-trimethyl

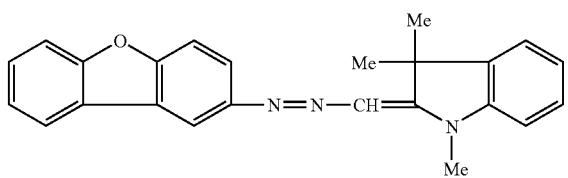

1H-Indole, 2-[(2-
dibenzofuranylazo)methylene]-2,3-
dihydro-1,3,3-trimethyl

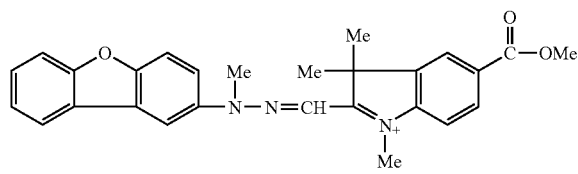

3H-Indolium methyl sulfate, 2-[(2-
dibenzofuranylmethylhydrazono)methyl]-
5-methoxycarbonyl)-1,3,3-trimethyl-,

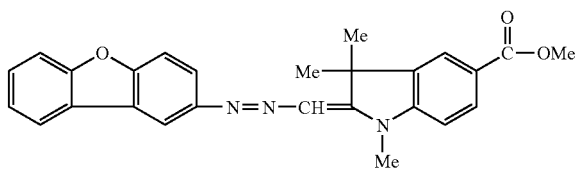

1H-Indole-5-carboxylic acid, 2-[(2-
dibenzofuranylazo)methylene]-2,3-
dihydro-1,3,3-trimethyl-, methyl ester -continued

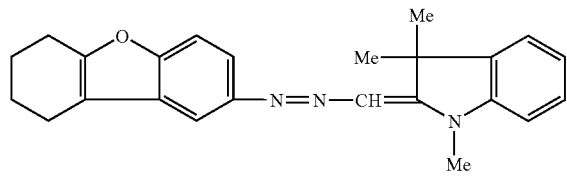

1H-Indole, 2,3-dihydro-1,3,3-trimethyl-2-
[[[(6,7,8,9-tetrahydro-2-
dibenzofuranyl)azo]methylene]

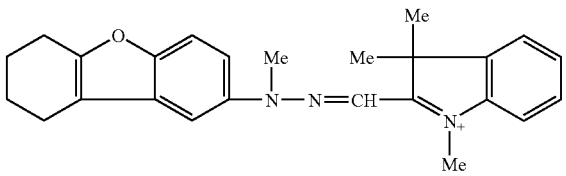

3H-Indolium trichlorozincate (1-), 1,3,3-
trimethyl-2-[[[methyl(6,7,8,9-tetrahydro-2-
dibenzofuranyl)hydrazono]methyl]-,

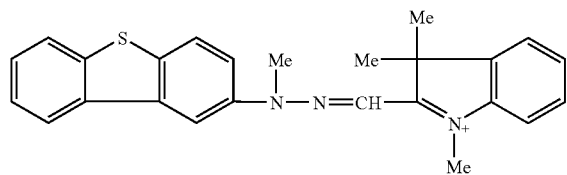

3H-Indolium methyl sulfate, 2-[(2-
dibenzothienylmethylhydrazono)methyl]-
1,3,3-trimethyl

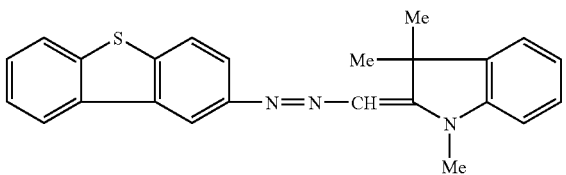

1H-Indole, 2-[(2-dibenzothienylazo)
methylene]-2,3-dihydro-1,3,3-trimethyl-

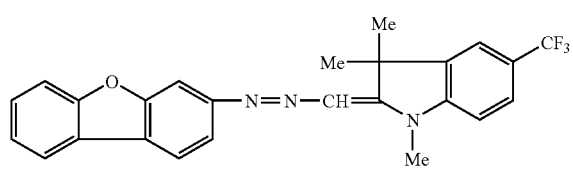

1H-Indole, 2-[(3-dibenzofuranylazo)
methylene]-2,3-dihydro-1,3,3-trimethyl-5-
(trifluoromethyl)-

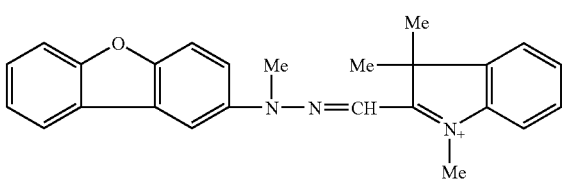

3H-Indolium methyl sulfate, 2-[(2-
dibenzofuranylmethylhydrazono)methyl]-
1,3,3-trimethyl

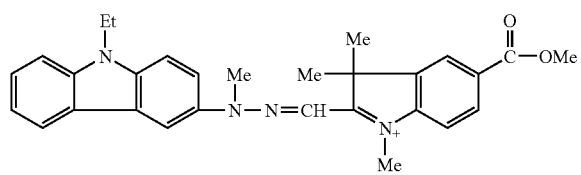

3H-Indolium methyl sulfate, 2-[[(9-ethyl-
9H-carbazol-3-yl)methylhydrazono]
methyl]-5-(methoxycarbonyl)-1,3,3-trimethyl

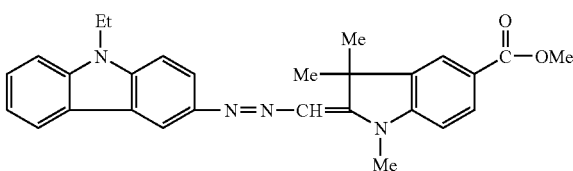

1H-Indole-5-carboxylic acid, 2-[[(9-ethyl-
9H-carbazol-3-yl)azo]methylene]-2,3-
dihydro-1,3,3-trimethyl-, methyl ester

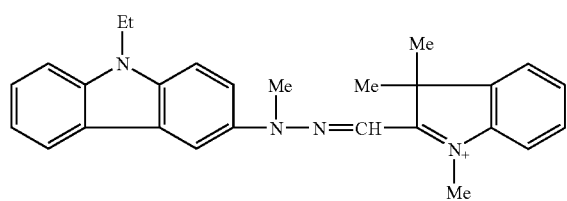

3H-Indolium 4-methylbenzenesulfonate,
2-[[(9-ethyl-9H-carbazol-3-yl)methyl-
hydrazono]methyl]-1,3,3-trimethyl

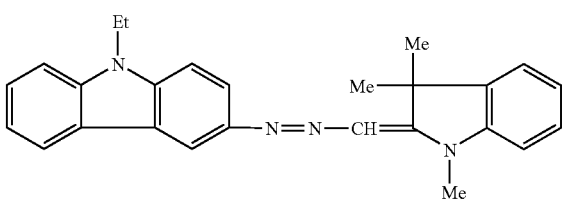

C9H-Carbazole, 3-[[[(1,3-dihydro-1,3,3-
trimethyl-2H-indol-2-ylidene)methyl]azo]-
9-ethyl- -continued

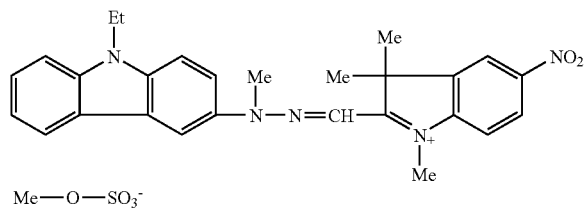

Me—O—SO₃⁻

3H-Indolium methyl sulfate, 2-[[(9-ethyl-
9H-carbazol-3-yl)methylhydrazono]
methyl]-1,3,3-trimethyl-5-nitro

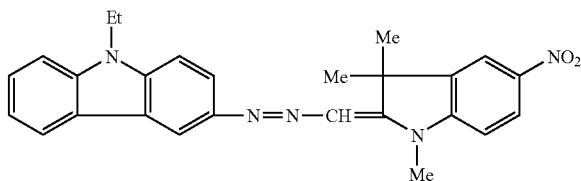

9H-Carbazole, 3-[[(1,3-dihydro-1,3,3-
trimethyl-5-nitro-2H-indol-2-
ylidene)methyl]azo]-9-ethyl-

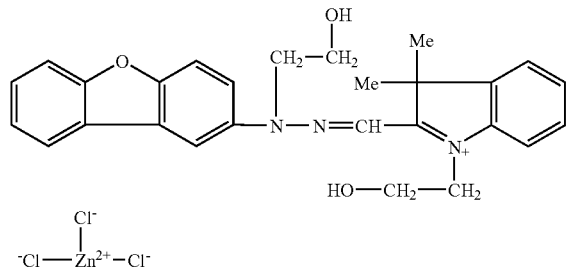

Cl⁻
⁻Cl—Zn²⁺—Cl⁻

3H-Indolium trichlorozincate, 2-[[2-
dibenzofuranyl(2-hydroxyethyl) hydrazono]
methyl]-1-(2-hydroxyethyl)-3,3-dimethyl

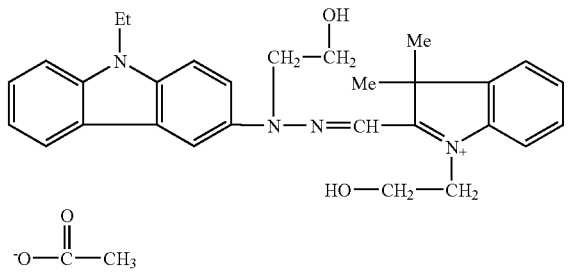

⁻O—C(=O)—CH₃

3H-Indolium acetate, 2-[[(9-ethyl-9H-
carbazol-3-yl)(2-hydroxyethyl)hydrazono]
methyl]-1-(2-hydroxyethyl)-3,3-dimethyl

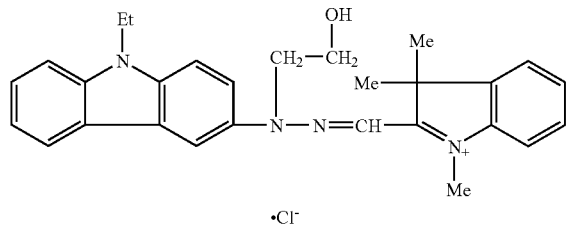

·Cl⁻

3H-Indolium chloride, 2-[[(9-ethyl-9H-
carbazol-3-yl)(2-hydroxyethyl)hydrazono]
methyl]-1,3,3-trimethyl

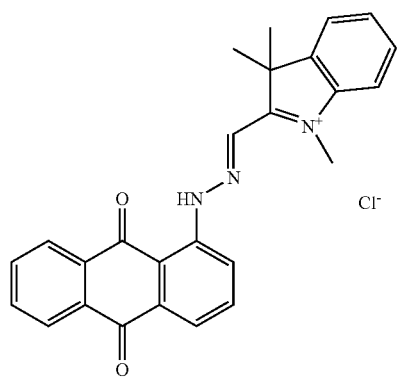

2-[(1-Anthraquinonyl hydrazono)methyl]-
1,3,3-trimethyl-3H-Indolium chloride

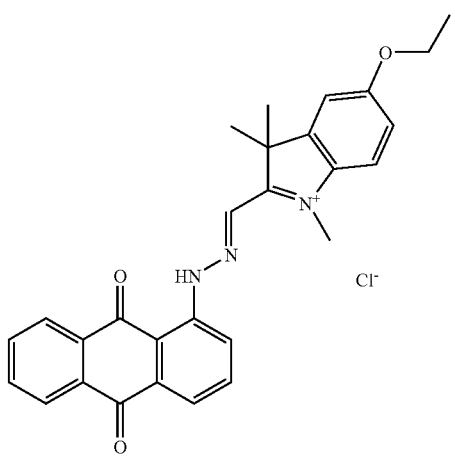

2-[(1-Anthraquinonylhydrazono) methyl]-
5-ethoxy-1,3,3-trimethyl-3H-Indolium chloride

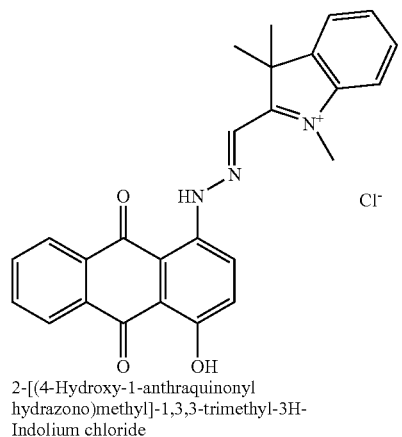

2-[(4-Hydroxy-1-anthraquinonyl hydrazono)methyl]-1,3,3-trimethyl-3H-Indolium chloride

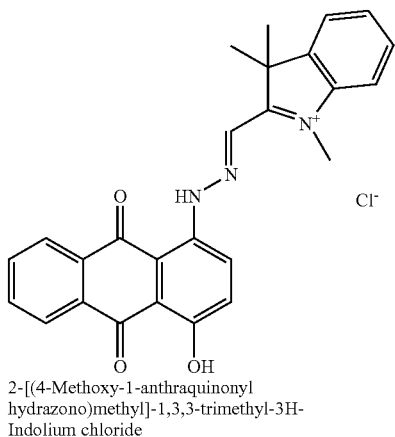

2-[(4-Methoxy-1-anthraquinonyl hydrazono)methyl]-1,3,3-trimethyl-3H-Indolium chloride

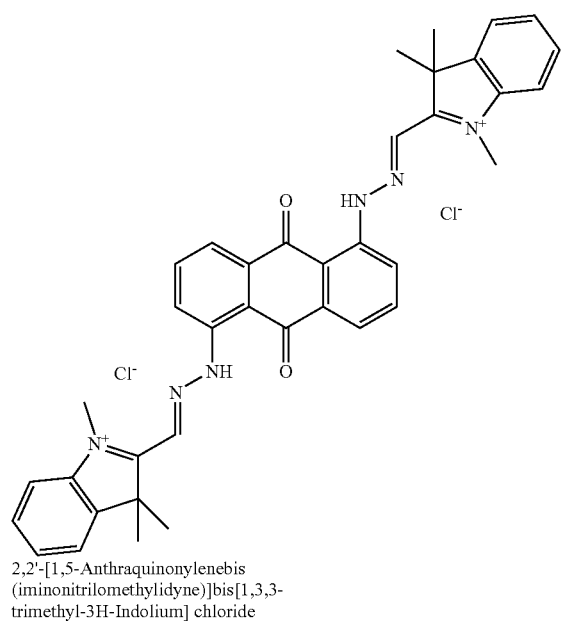

2,2'-[1,5-Anthraquinonylenebis (iminonitrilomethylidyne)]bis[1,3,3-trimethyl-3H-Indolium] chloride

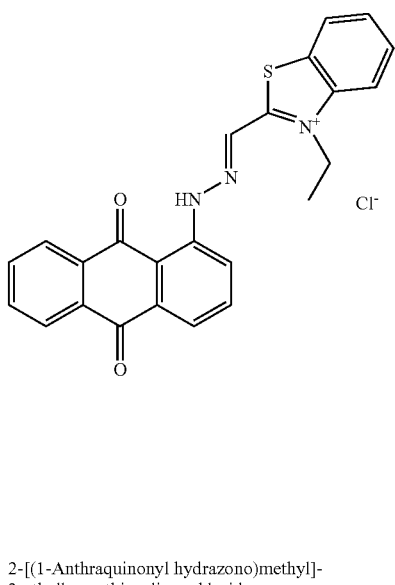

2-[(1-Anthraquinonyl hydrazono)methyl]-3-ethylbenzothiazolium chloride

It is to be understood that the nature of the counterions present in the above table, when specified, is simply given as a guide and that, in the context of the present disclosure, it is envisaged that all the dyes mentioned above may be associated with the counterions X as defined above.

The compounds used in the context of the present disclosure may be obtained, for example, from an aldehyde or ketone and a hydrazine derivative in two steps: condensation followed by quaternization.

The compounds used in the present disclosure may also be obtained from an activated methylene and a diazonium salt derivative in one step.

In accordance with one embodiment of the present disclosure, the at least one direct dye of formula (I) is present in the composition in an amount ranging from 0.001% to 5% by weight relative to the total weight of the dye composition, for example, from 0.05% to 2% by weight relative to the total weight of the dye composition.

Thickeners

As indicated previously, the dye composition according to the present disclosure further comprises at least one cosmetic agent chosen from thickening polymers (thickeners) and surfactants. As used herein, the term "thickener" means any agent known for increasing the viscosity when it is placed in an aqueous medium. For instance, the at least one thickener may increase the viscosity of an aqueous medium by at least 50 cps at 25° C. at a shear rate of 1 s$^{-1}$ if present at 1% by weight of active material.

The thickeners useful herein may be chosen, for example, from:
(i) associative thickeners;
(ii) crosslinked acrylic acid homopolymers;
(iii) crosslinked copolymers of (meth)acrylic acid and of $(C_1-C_6)$alkyl acrylate;
(iv) nonionic homopolymers and copolymers containing ethylenically unsaturated monomers of ester and/or amide type;
(v) ammonium acrylate homopolymers or copolymers of ammonium acrylate and of acrylamide;
(vi) polysaccharides;
(vii) $C_{12}-C_{30}$ fatty alcohols;
(viii) mineral thickeners; and
mixtures thereof.

(i) As used herein, the expression "associative thickener" means an amphiphilic thickener comprising both hydrophilic units and hydrophobic units, for instance, comprising at least one $C_8$-$C_{30}$, for example, $C_{10}$-$C_{30}$, fatty chain. In at least one embodiment, the fatty chain may be an alkyl chain or may comprise an alkyl chain.

Associative thickeners suitable for use according to the present disclosure may be chosen, for example, from:
(a) nonionic amphiphilic polymers comprising at least one fatty chain and at least one hydrophilic unit;
(b) anionic amphiphilic polymers comprising at least one hydrophilic unit and at least one fatty-chain unit;
(c) cationic amphiphilic polymers comprising at least one hydrophilic unit and at least one fatty-chain unit; and
(d) amphoteric amphiphilic polymers comprising at least one hydrophilic unit and at least one fatty-chain unit.

Examples of nonionic amphiphilic polymers comprising at least one fatty chain and at least one hydrophilic unit include, but are not limited to:
(1) celluloses modified with groups comprising at least one fatty chain, for example:
hydroxyethylcelluloses modified with groups comprising at least one fatty chain, such as alkyl, arylalkyl, and alkylaryl groups, and mixtures thereof, and in at least one embodiment, in which the alkyl groups may be chosen from $C_8$-$C_{22}$ alkyl groups. In another embodiment, the fatty chain is a $C_8$-$C_{22}$ alkyl chain. Non-limiting examples of products of this type include NATROSOL PLUS Grade 330 CS ($C_{16}$ alkyls) sold by the company Aqualon, and BERMOCOLL EHM 100 sold by the company Berol Nobel, and
celluloses modified with polyalkylene glycol alkylphenyl ether groups, such as the product AMERCELL POLYMER HM-1500 (polyethylene glycol (15) nonylphenyl ether) sold by the company Amerchol,
(2) hydroxypropyl guars modified with groups comprising at least one fatty chain, such as the product ESAFLOR HM 22 ($C_{22}$ alkyl chain) sold by the company Lamberti, and the products MIRACARE XC95-3 ($C_{14}$ alkyl chain) and RE205-1 ($C_{20}$ alkyl chain) sold by the company Rhodia Chimie,
(3) polyether urethanes comprising at least one fatty chain, such as $C_{10}$-$C_{30}$ alkyl and alkenyl groups, for instance, the products DAPRAL T 210 and DAPRAL T 212 sold by the company Akzo and the products ACULYN 44 and ACULYN 46 sold by the company Rohm & Haas,
(4) copolymers of vinylpyrrolidone and of hydrophobic fatty-chain monomers, for example:
the products ANTARON V216 and GANEX V216 (vinylpyrrolidone/hexadecene copolymer) sold by the company I.S.P., and
the products ANTARON V220 and GANEX V220 (vinylpyrrolidone/eicosene copolymer) sold by the company I.S.P.,
(5) copolymers of $C_1$-$C_6$ alkyl acrylates and methacrylates and of amphiphilic monomers comprising at least one fatty chain, for example, the oxyethylenated methyl methacrylate/stearyl acrylate copolymer sold by the company Goldschmidt under the name ANTIL 208,
(6) copolymers of hydrophilic acrylates and methacrylates and of hydrophobic monomers comprising at least one fatty chain, for example, polyethylene glycol methacrylate/lauryl methacrylate copolymers.

Examples of anionic amphiphilic polymers comprising at least one hydrophilic unit and at least one fatty-chain unit, include, but are not limited to, those comprising at least one fatty-chain allyl ether unit and at least one hydrophilic unit comprising at least one ethylenic unsaturated anionic monomer, for instance, vinylcarboxylic acid, and in one embodiment, chosen from acrylic acids, methacrylic acids, and mixtures thereof. In another embodiment, the fatty-chain allyl ether unit may be chosen from monomers of formula (V):

$$CH_2=C(R_1)CH_2OB_nR \qquad (V)$$

wherein $R_1$ is chosen from H and $CH_3$, B is an ethyleneoxy radical, n is an integer ranging from 0 to 100, and R is a hydrocarbon-based radical chosen from alkyl, arylalkyl, aryl, alkylaryl, and cycloalkyl radicals, comprising from 10 to 30 carbon atoms, for example, from 10 to 24 carbon atoms, or from 12 to 18 carbon atoms.

In at least one embodiment, in the unit of formula (V), $R_1$ is H, n is equal to 10, and R is a stearyl ($C_{18}$) radical. Anionic amphiphilic polymers of this type are described and prepared, according to an emulsion polymerization process, for example, in European Patent Application No. 0 216 479.

The anionic amphiphilic polymers described above may be chosen, for example, from polymers formed from 20% to 60% by weight of acrylic acid and/or of methacrylic acid, from 5% to 60% by weight of lower alkyl (meth)acrylates, from 2% to 50% by weight of fatty-chain allyl ether of formula (V), and from 0% to 1% by weight of a crosslinking agent chosen from known copolymerizable unsaturated polyethylenic monomers, for instance, diallyl phthalate, allyl (meth)acrylate, divinylbenzene, (poly)ethylene glycol dimethacrylate, and methylenebisacrylamide.

Non-limiting examples of the anionic amphiphilic polymers described above include, but are not limited to, crosslinked terpolymers of methacrylic acid, of ethyl acrylate and of polyethylene glycol (10 EO) stearyl ether (Steareth-10), such as those sold by the company Ciba under the names SALCARE SC 80 and SALCARE SC 90, which are aqueous 30% emulsions of a crosslinked terpolymer of methacrylic acid, of ethyl acrylate and of steareth-10 allyl ether (40/50/10).

The anionic amphiphilic polymers may also be chosen, for instance, from those comprising at least one hydrophilic unit of unsaturated olefinic carboxylic acid type, and at least one hydrophobic unit of the type such as a ($C_{10}$-$C_{30}$) alkyl ester of an unsaturated carboxylic acid. In at least one embodiment, the polymers may be chosen from those in which the hydrophilic unit of unsaturated olefinic carboxylic acid type is chosen from monomers of formula (VI):

(VI)

wherein $R^1$ is chosen from H, $CH_3$, and $C_2H_5$, i.e., acrylic acid, methacrylic acid, and ethacrylic acid units, and in which the hydrophobic unit of the type such as a ($C_{10}$-$C_{30}$) alkyl ester of an unsaturated carboxylic acid is chosen from monomers of formula (VII):

$$H_2C=CR^1—CO—OR^2 \qquad (VII)$$

wherein $R^1$ is chosen from H, $CH_3$, and $C_2H_5$ (i.e. acrylate, methacrylate, and ethacrylate units), and in at least one embodiment, chosen from H and $CH_3$, and $R^2$ is chosen from $C_{10}$-$C_{30}$, for example, $C_{12}$-$C_{22}$, alkyl radicals.

($C_{10}$-$C_{30}$) Alkyl esters of unsaturated carboxylic acids in accordance with the present disclosure include, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic amphiphilic polymers of this type and the preparation thereof are disclosed, for example, in U.S. Pat. Nos. 3,915,921 and 4,509,949.

The anionic amphiphilic polymers described above that may be used in accordance with the present disclosure may be chosen, in at least one embodiment, from polymers formed from a mixture of monomers comprising:
(i) essentially acrylic acid, an ester of formula (VIII) below:

$$H_2C=CR^1-CO-OR^2 \quad (VIII)$$

wherein $R^1$ is chosen from H and $CH_3$, $R^2$ is chosen from alkyl radicals comprising from 12 to 22 carbon atoms, and a crosslinking agent, for example, those comprising of from 60% to 95% by weight of acrylic acid (hydrophilic unit), 4% to 40% by weight of $C_{10}$-$C_{30}$ alkyl acrylate (hydrophobic unit), and 0% to 6% by weight of crosslinking polymerizable monomer, or 96% to 98% by weight of acrylic acid (hydrophilic unit), 1% to 4% by weight of $C_{10}$-$C_{30}$ alkyl acrylate (hydrophobic unit), and
(ii) essentially acrylic acid and lauryl methacrylate, such as the product formed from 66% by weight of acrylic acid and 34% by weight of lauryl methacrylate.

These polymers may be crosslinked using at least one crosslinking agent. The at least one crosslinking agent may be chosen from compounds comprising the group

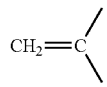

with at least one other polymerizable group whose unsaturated bonds are not conjugated. Non-limiting examples include polyallyl ethers such as polyallylsucrose and polyallylpenta-erythritol.

Examples of commercial products corresponding to the polymers described above include, but are not limited to, the products sold by the company Goodrich under the trade names PEMULEN TR1, PEMULEN TR2, and CARBOPOL 1382, and the product sold by the company S.E.P.C. under the name COATEX SX. In at least one embodiment, the at least one thickening polymer is PEMULEN TR1.

A further non-limiting example of an anionic amphiphilic fatty-chain polymer is the ethoxylated copolymer of methacrylic acid/methyl acrylate/alkyl dimethyl-meta-isoprepenylbenzylisocyanate sold under the name VISCOPHOBE DB 1000 by the company Amerchol.

The cationic amphiphilic polymers which may be used in accordance with the present disclosure may be chosen, for example, from quaternized cellulose derivatives and polyacrylates containing amino side groups.

Suitable quaternized cellulose derivatives include, for example:
  quaternized celluloses modified with groups comprising at least one fatty chain, such as alkyl, arylalkyl, and alkylaryl groups comprising at least 8 carbon atoms, and mixtures thereof, and
  quaternized hydroxyethylcelluloses modified with groups comprising at least one fatty chain, such as alkyl, arylalkyl and alkylaryl groups, and in at least one embodiment, alkyl groups, comprising at least 8 carbon atoms, and mixtures thereof.

Quaternized or non-quaternized polyacrylates containing amino side groups, may comprise, for example, hydrophobic groups, and may be chosen, for instance, from Steareth 20 (polyoxyethylenated(20) stearyl alcohol) and ($C_{10}$-$C_{30}$)alkyl PEG-20 itaconate.

In at least one embodiment, the alkyl radicals borne by the above quaternized celluloses and hydroxyethylcelluloses comprise from 8 to 30 carbon atoms.

In another embodiment, the aryl radicals may be chosen from phenyl, benzyl, naphthyl, and anthryl groups.

Examples of quaternized alkylhydroxyethylcelluloses containing $C_8$-$C_{30}$ fatty chains which may be used in accordance with the present disclosure include, but are not limited to, the products QUATRISOFT LM 200, QUATRISOFT LM-X 529-18-A, QUATRISOFT LM-X 529-18B ($C_{12}$ alkyl), and QUATRISOFT LM-X 529-8 ($C_{18}$ alkyl) sold by the company Amerchol, and the products CRODACEL QM, CRODACEL QL ($C_{12}$ alkyl), and CRODACEL QS ($C_{18}$ alkyl) sold by the company Croda.

Examples of polyacrylates containing amino side chains include, for instance, the polymers 8781-124B and 9492-103 and STRUCTURE PLUS from the company National Starch.

Suitable amphoteric amphiphilic polymers containing at least one fatty chain may be chosen, for instance, from copolymers of methacrylamidopropyltrimethylammonium chloride/acrylic acid/$C_{10}$-$C_{30}$ alkyl methacrylate. In at least one embodiment, the alkyl radical is a stearyl radical.

(ii) Examples of crosslinked acrylic acid homopolymers include, but are not limited to, those crosslinked with an allylic alcohol ether of the sugar series, for example, the products sold under the names CARBOPOL 980, 981, 954, 2984, and 5984 by the company Goodrich and the products sold under the names SYNTHALEN M and SYNTHALEN K by the company 3 VSA.

(iii) Crosslinked copolymers of (meth)acrylic acid and of $C_1$-$C_6$ alkyl acrylate may be chosen, for example, from the product sold under the name VISCOATEX 538C by the company Coatex, which is a crosslinked copolymer of methacrylic acid and of ethyl acrylate as an aqueous dispersion containing 38% active material, and the product sold under the name ACULYN 33 by the company Rohm & Haas, which is a crosslinked copolymer of acrylic acid and of ethyl acrylate as an aqueous dispersion containing 28% active material.

(iv) Examples of nonionic homopolymers and copolymers containing ethylenically unsaturated monomers of ester and/or amide type include, but are not limited to, the products sold under the names: CYANAMER P250 by the company Cytec (polyacrylamide); PMMA MBX-8C by the company US Cosmetics (methyl methacrylate/ethylene glycol dimethacrylate copolymer); ACRYLOID B66 by the company Rohm & Haas (butyl methacrylate/methyl methacrylate copolymer); and BPA 500 by the company Kobo (polymethyl methacrylate).

(v) A non-limiting example of a suitable ammonium acrylate homopolymer is the product sold under the name MICROSAP PAS 5193 by the company Hoechst.

Copolymers of ammonium acrylate and of acrylamide may include, for example, the product sold under the name BOZEPOL C NOUVEAU and the product PAS 5193 sold by the company Hoechst, which are described and prepared, for instance, in French Patent No. 2 416 723 and U.S. Pat. Nos. 2,798,053 and 2,923,692).

(vi) Thickening polysaccharides may be chosen from glucans, modified or unmodified starches (such as those derived, for example, from cereals, for instance, wheat, corn, and rice, from vegetables, for instance, yellow pea, and tubers, for instance, potato and cassava), amylose, amylopectin, glycogen, dextrans, celluloses and derivatives thereof (methylcelluloses, hydroxyalkylcelluloses, ethylhydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids, pectins, alginic acid, alginates, arabinogalactans, carrageenans, agars, glycosaminoglucans, gum arabics, gum tragacanths, ghatti gums, karaya gums, carob gums, galactomannans such as guar gums and nonionic derivatives thereof (hydroxypropyl guar), xanthan gums, and mixtures thereof.

The compounds of this type that may be used in accordance with the present disclosure may be chosen from those described, for example, in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums—Polysaccharides and their Derivatives", edited by Roy L. Whistler, Second Edition, published by Academic Press Inc., the content of these three publications being incorporated herein by reference in their entireties.

In at least one embodiment, the polysaccharides may be chosen from starches, guar gums, celluloses, and derivatives thereof.

The guar gums may be modified or unmodified.

The unmodified guar gums may include, for example, the products sold under the name VIDOGUM GH 175 by the company Unipectine and under the names MEYPRO-GUAR 50 and JAGUAR C by the company Meyhall.

The modified nonionic guar gums may be modified, for example, with $C_1$-$C_6$ hydroxyalkyl groups.

Examples of hydroxyalkyl groups include, but are not limited to, hydroxymethyl, hydroxyethyl, hydroxypropyl, and hydroxybutyl groups.

These guar gums are well known in the prior art and can be prepared, for example, by reacting the corresponding alkene oxides, for example, propylene oxides, with the guar gum so as to obtain a guar gum modified with hydroxyalkyl, for instance, hydroxypropyl, groups.

The degree of hydroxyalkylation, which corresponds to the number of alkylene oxide molecules consumed by the number of free hydroxyl functions present on the guar gum, may range from 0.4 to 1.2.

Such nonionic guar gums optionally modified with hydroxyalkyl groups are sold, for example, under the trade names JAGUAR HP8, JAGUAR HP60, JAGUAR HP120, JAGUAR DC 293, and JAGUAR HP 105 by the company Rhodia Chimie (Meyhall) and under the name GALACTASOL 4H4FD2 by the company Aqualon.

Examples of suitable celluloses and derivatives thereof include celluloses modified with $C_1$-$C_6$ hydroxyalkyl groups, for instance, hydroxyethylcelluloses and hydroxypropylcelluloses, such as the products sold under the names KLUCEL EF, KLUCEL H, KLUCEL LHF, KLUCEL MF, and KLUCEL G by the company Aqualon.

In at least one embodiment, the fatty alcohols may be chosen from monohydroxylated alcohols, which may be saturated, comprising from 8 to 30 carbon atoms, for instance myristyl alcohol, cetyl alcohol, stearyl alcohol, and behenyl alcohol.

Mineral thickeners, for example, clays, may also be used.

In another embodiment, the at least one thickener of the present disclosure is an organic polymer.

According to the present disclosure, the at least one thickener is present in the composition in an amount ranging from 0.001% to 20% by weight, for example, from 0.01% to 10% by weight, or from 0.1% to 3% by weight, relative to the total weight of the dye composition.

Surfactants

When the composition of the present disclosure contains at least one surfactant, this surfactant may be chosen from anionic, amphoteric, non-ionic, and cationic surfactants, and mixtures thereof.

Examples of surfactants that are suitable for carrying out the present disclosure include, but are not limited to:

(i) Anionic Surfactant(s):

Examples of anionic surfactants which can be used in accordance with the present disclosure include, but are not limited to salts (for example, alkali-metal salts and alkaline-earth metal salts, such as sodium salts, magnesium salts, ammonium salts, amine salts, and amino alcohol salts) of alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates; N-acyltaurates; and mixtures thereof.

Other examples of suitable anionic surfactants include, but are not limited to, salts of saturated or unsaturated fatty acids comprising from 8 to 30 carbon atoms and optionally hydroxylated, such as the salts of oleic, ricinoleic, palmitic and stearic acids, coconut oil acid, and hydrogenated coconut oil acid; and acyl lactylates.

In at least one embodiment, the alkyl or acyl radicals of all these various compounds comprises from 8 to 24 carbon atoms. In another embodiment, the aryl radicals may be chosen from phenyl and benzyl groups.

Weakly anionic surfactants can also be used herein, such as ($C_6$-$C_{24}$)alkyl-D-galactosiduronic acids and their salts, polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, and in at least one embodiment, those comprising from 2 to 50 ethylene oxide groups, and mixtures thereof.

According to one embodiment, the anionic surfactants may be chosen from alkyl sulfate salts and alkyl ether sulfate salts and mixtures thereof.

(ii) Nonionic Surfactant(s):

The nonionic surfactants may be chosen from compounds that are known in the art (see, for example, "Handbook of Surfactants" by M. R. Porter, published by Blackie & Son (Glasgow and London), 1991, pp. 116-178).

The nonionic surfactants may, for instance, be chosen from polyethoxylated, polypropoxylated, and polyglycerolated alcohols; polyethoxylated, polypropoxylated, and polyglycerolated α-diols; polyethoxylated, polypropoxylated, and polyglycerolated alkylphenols; and polyethoxylated, polypropoxylated, and polyglycerolated fatty acids; these compounds having a fatty chain, for instance, an alkyl chain, comprising, for example, from 8 to 18 carbon atoms, wherein the number of ethylene oxide or propylene oxide groups may range, for example, from 2 to 50 and the number of glycerol groups may range, for example, from 2 to 30.

Other examples of suitable nonionic surfactants include, but are not limited to, copolymers of ethylene oxide and of propylene oxide; condensates of ethylene oxide and of propylene oxide with fatty alcohols, for example, saturated or unsaturated, mono- or polyhydroxylated $C_8$-$C_{30}$ fatty alcohols; polyethoxylated fatty amides, for instance, saturated or unsaturated $C_8$-$C_{30}$ fatty amides, comprising, for example, from 2 to 30 mol of ethylene oxide; polyglycerolated fatty amides, such as saturated or unsaturated $C_8$-$C_{30}$ fatty amides, comprising on average from 1 to 5, for instance, from 1.5 to 4, glycerol groups; oxyethylenated fatty acid esters of sorbitan, for example, saturated or unsaturated $C_8$-$C_{30}$ fatty acids, comprising from 2 to 30 mol of ethylene oxide; fatty acid esters of sucrose, for instance, saturated or unsaturated $C_8$-$C_{30}$ fatty acids; fatty acid esters of polyethylene glycol, for example, saturated or unsaturated $C_8$-$C_{30}$ fatty acids; ($C_8$-$C_{30}$)alkylpolyglycosides, N—($C_8$-$C_{30}$)alkylglucamine derivatives, and amine oxides such as ($C_{10}$-$C_{14}$)alkylamine oxides and N—($C_8$-$C_{30}$)acylaminopropylmorpholine oxides.

In at least one embodiment, the nonionic surfactants are alkylpolyglycosides.

(iii) Amphoteric Surfactant(s):

The amphoteric surfactants may be chosen, for example, from aliphatic secondary or tertiary amine derivatives in which the aliphatic radical is a linear or branched chain comprising from 8 to 22 carbon atoms and at least one water-soluble anionic group (for example, carboxylate, sulfonate, sulfate, phosphate, and phosphonate); ($C_8$-$C_{20}$)alkylbetaines, sulfobetaines; ($C_8$-$C_{20}$)alkylamido($C_1$-$C_6$)alkylbetaines; and ($C_8$-$C_{20}$)alkylamido($C_1$-$C_6$)alkylsulfobetaines.

Examples of suitable amine derivatives include, but are not limited to, the products sold under the name MIRANOL, and described, for example, in U.S. Pat. Nos. 2,528,378 and 2,781,354, and having the structures:

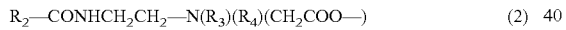

$$R_2-CONHCH_2CH_2-N(R_3)(R_4)(CH_2COO-) \quad (2)$$

wherein: $R_2$ is chosen from linear or branched $C_5$-$C_{20}$ alkyl radicals derived from an acid $R_2$—COOH present in hydrolyzed coconut oil, heptyl radicals, nonyl radicals, and undecyl radicals, $R_3$ is a β-hydroxyethyl group, and $R_4$ is a carboxymethyl group; and

$$R_5-CONHCH_2CH_2-N(B)(C) \quad (3)$$

wherein B is —$CH_2CH_2OX'$, C is —$(CH_2)_z$—Y', z is equal to 1 or 2, X' is chosen from —$CH_2CH_2$—COOH and hydrogen, Y' is chosen from —COOH and —$CH_2$—CHOH—$SO_3H$, and $R_5$ is a linear or branched, saturated or unsaturated $C_5$-$C_{20}$ alkyl radical of an acid $R_5$—COOH present in, for example, coconut oil and hydrolyzed linseed oil.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid.

A non-limiting example of a suitable amphoteric surfactant is the cocoamphodiacetate sold under the trade name MIRANOL C2M Concentrate by the company Rhodia Chimie.

(iv) Cationic Surfactant(s):

The cationic surfactants may be chosen, for example, from:
A) quaternary ammonium salts of formula (XII):

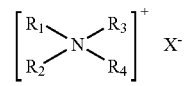

(XII)

wherein:
$X^-$ is an anion chosen from halides (e.g., chloride, bromide, and iodide); ($C_2$-$C_6$)alkyl sulfates, for instance, methyl sulfate; phosphates; alkyl sulfonates; alkylaryl sulfonates; and anions derived from organic acid, such as acetate and lactate; and
i) the radicals $R_1$, $R_2$, and $R_3$, which may be identical or different, are chosen from linear or branched aliphatic radicals comprising from 1 to 4 carbon atoms and aromatic radicals such as aryl and alkylaryl. The aliphatic radicals may comprise heteroatoms such as oxygen, nitrogen, sulfur, and halogen atoms. In at least one embodiment, the aliphatic radicals are chosen, for example, from alkyl, alkoxy, and alkylamide radicals, and
$R_4$ is a linear or branched alkyl radical comprising from 16 to 30 carbon atoms. Non-limiting examples of cationic surfactants corresponding to the above definition include behenyltrimethylammonium salts (for example, chlorides); or
ii) the radicals $R_1$ and $R_2$, which may be identical or different, are chosen from linear or branched aliphatic radicals comprising from 1 to 4 carbon atoms and aromatic radicals such as aryl and alkylaryl. The aliphatic radicals may comprise heteroatoms such as oxygen, nitrogen, sulfur, and halogen atoms. In at least one embodiment, the aliphatic radicals are chosen, for example, from alkyl, alkoxy, alkylamide, and hydroxyalkyl radicals comprising from about 1 to 4 carbon atoms; and
$R_3$ and $R_4$, which may be identical or different, are chosen from linear or branched alkyl radicals comprising from 12 to 30 carbon atoms, wherein the radical comprises at least one function chosen from ester and amide functions;

In at least one embodiment, $R_3$ and $R_4$ are chosen from ($C_{12}$-$C_{22}$)alkylamido($C_2$-$C_6$)alkyl and ($C_{12}$-$C_{22}$)alkylacetate radicals.

Non-limiting examples of cationic surfactants corresponding to the above definition include stearamidopropyldimethyl (myristyl acetate)ammonium salts (for example, chlorides);
B) quaternary ammonium salts of imidazolinium, for example, those of formula (XIII):

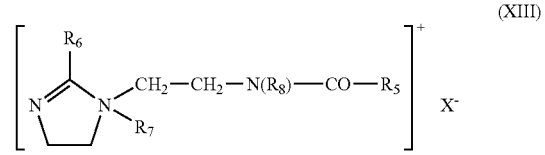

(XIII)

wherein $R_5$ is chosen from alkenyl and alkyl radicals comprising from 8 to 30 carbon atoms, for example, fatty acid derivatives of tallow, $R_6$ is chosen from hydrogen, $C_1$-$C_4$ alkyl radicals, and alkenyl and alkyl radical comprising from 8 to 30 carbon atoms, $R_7$ is a $C_1$-$C_4$ alkyl radical, $R_8$ is chosen from hydrogen and $C_1$-$C_4$ alkyl radicals, and X is an anion chosen from halides, phosphates, acetates, lactates, alkyl sulfates, alkyl sulfonates, and alkylaryl sulfonates. In at least one embodiment, $R_5$ and $R_6$ are chosen from mixtures of alkenyl and alkyl radicals comprising from 12 to 21 carbon atoms, for example, fatty acid derivatives of tallow, $R_7$ is methyl, and $R_8$ is hydrogen. Such a definition includes, for example, Quaternium-27 (CTFA 1997) and Quaternium-83 (CTFA 1997), which are sold under the names "Rewoquat" W75, W90, W75PG, and W75HPG by the company Witco, C) diquaternary ammonium salts of formula (XIV):

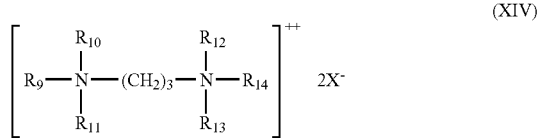

(XIV)

wherein $R_9$ is an aliphatic radical comprising from 16 to 30 carbon atoms, $R_{10}$, $R_{11}$, $R_{12}$, $R_{13}$, and $R_{14}$, which may be identical or different, are chosen from hydrogen and alkyl radicals comprising from 1 to 4 carbon atoms, and X is an anion chosen from halides, acetates, phosphates, nitrates, and methyl sulfates. A non-limiting example of a cationic surfactant corresponding to the above definition is propanetallow-diammonium dichloride;

D) quaternary ammonium salts comprising at least one ester function, for example, those of formula (XV):

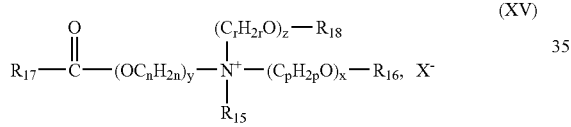

(XV)

wherein:
$R_{15}$ is chosen from $C_1$-$C_6$ alkyl radicals, $C_1$-$C_6$ hydroxyalkyl radicals, and $C_1$-$C_6$ dihydroxyalkyl radicals;
$R_{16}$ is chosen from:
$R_{19}$—CO— radicals,
linear or branched, saturated or unsaturated $C_1$-$C_{22}$ hydrocarbon-based radicals $R_{20}$, and
hydrogen,
$R_{18}$ is chosen from:
$R_{21}$—CO— radials
linear or branched, saturated or unsaturated $C_1$-$C_6$ hydrocarbon-based radicals $R_{22}$, and
hydrogen,
$R_{17}$, $R_{19}$, and $R_{21}$, which may be identical or different, are chosen from linear or branched, saturated or unsaturated $C_7$-$C_{21}$ hydrocarbon-based radicals;
n, p, and r, which may be identical or different, are integers ranging from 2 to 6;
y is an integer ranging from 1 to 10;
x and z, which may be identical or different, are integers ranging from 0 to 10; and
$X^-$ is a simple or complex, organic or inorganic anion;

with the provisos that the sum x+y+z ranges from 1 to 15, when x is 0, then $R_{16}$ has the same definition as $R_{20}$, and when z is 0, then $R_{18}$ has the same definition as $R_{22}$.

In at least one embodiment, the cationic surfactants are chosen from ammonium salts of formula (XV), wherein:

$R_{15}$ is chosen from methyl and ethyl radicals,
x and y are equal to 1;
z is equal to 0 or 1;
n, p, and r are equal to 2;
$R_{16}$ is chosen from:
$R_{19}$—CO— radicals,
methyl, ethyl, or $C_{14}$-$C_{22}$ hydrocarbon-based radicals, and hydrogen;
$R_{17}$, $R_{19}$, and $R_{21}$, which may be identical or different, are chosen from linear or branched, saturated or unsaturated $C_7$-$C_{21}$ hydrocarbon-based radicals;
$R_{18}$ is chosen from:
$R_{21}$—CO— radicals, and
hydrogen.

Such compounds are sold, for example, under the names DEHYQUART by the company Cognis, STEPANQUAT by the company Stepan, NOXAMIUM by the company Ceca, and REWOQUAT WE 18 by the company Rewo-Witco.

According to at least one embodiment, the quaternary ammonium salts may be chosen from behenyltrimethylammonium chloride and stearamidopropyldimethyl(myristyl acetate)ammonium chloride, sold under the name "CERAPHYL 70" by the company Van Dyk, and Quaternium-27 or Quaternium-83 sold by the company Witco.

In another embodiment, the at least one surfactant is an anionic surfactant chosen from sodium, triethanolamine, and ammonium ($C_{12}$-$C_{14}$)alkyl sulfates; sodium, triethanolamine, and ammonium ($C_{12}$-$C_{14}$)alkyl ether sulfates oxyethylenated with 2.2 mol of ethylene oxide; sodium cocoyl isethionate; sodium α-($C_{14}$-$C_{16}$)olefin sulfonate; and mixtures thereof, with:
either an amphoteric surfactant such as the amine derivatives known as disodium cocoamphodipropionate and sodium cocoamphopropionate sold, for example, by the company Rhodia Chimie under the trade name "Miranol® C2M CONC" as an aqueous solution containing 38% active material, and under the name Miranol® C32;
or an amphoteric surfactant such as alkylbetaines, for instance, the cocobetaine sold under the name "Dehyton® AB 30" as an aqueous solution containing 32% AM by the company Cognis, and ($C_8$-$C_{20}$)alkylamido ($C_1$-$C_6$)alkylbetaines, for example, Tegobetaine® F50 sold by the company Goldschmidt.

In at least one embodiment, the at least one surfactant is present in the composition in an amount ranging from 0.1% to 60% by weight, for instance, from 3% to 40% by weight, or from 5% to 30% by weight relative to the total weight of the composition.

Additional Direct Dyes

The dye composition according to the present disclosure may optionally comprise at least one additional direct dye other than the compounds of formula (I). This dye may be chosen, for instance, from cationic and nonionic direct dyes.

Non-limiting examples of additional direct dyes include nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, natural dyes, and mixtures thereof.

Examples of azo direct dyes that may be used according to the present disclosure include, but are not limited to, the cationic azo dyes described in International Patent Application Publication Nos. WO 95/15144, WO 95/01772, WO 02/078 660, WO 02/100 834, and WO 02/100 369, European Patent Application No. 0 714 954, and French Patent Application Nos. 2 822 696, 2 825 702, 2 825 625, 2 822 698, 2 822 693, 2 822 694, 2 829 926, 2 807 650, and 2 844 269.

Suitable natural direct dyes that may be used according to the present disclosure include, for example, lawsone, juglone, alizarin, purpurin, carminic acid, kermesic acid, purpurogallin, protocatechaldehyde, indigo, isatin, curcumin, spinulosin, and apigenidin. Extracts and decoctions containing these natural dyes may also be used, for instance, henna-based poultices and extracts.

When present, the at least one additional direct dye is present in the composition in an amount ranging from 0.001% to 20% by weight relative to the total weight of the composition, for example, from 0.005% to 10% by weight relative to the total weight of the composition.

Oxidation Bases

The dye composition of the present disclosure may further comprise at least one oxidation base.

The at least one oxidation bases may be chosen from oxidation bases conventionally used in oxidation dyeing, for example para-phenylenediamines, bis(phenyl)alkylenediamines, para-aminophenols, ortho-aminophenols and heterocyclic bases.

Examples of suitable para-phenylenediamines include, but are not limited to, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N, N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

In at least one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl- para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Suitable bis(phenyl)alkylenediamines include, for example, N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylene-diamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and the acid addition salts thereof.

Non-limiting examples of para-aminophenols include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylamino-methyl)phenol, 4-amino-2-fluorophenol, and the acid addition salts thereof.

The ortho-aminophenols may be chosen, for example, from 2-aminophenol, 2-amino-5-methylphenol, 2-amino-6-methylphenol, and 5-acetamido-2-aminophenol, and the acid addition salts thereof.

Examples of heterocyclic bases include, for example, pyridine derivatives, pyrimidine derivatives, pyrazole derivatives, and derivatives of pyrazolo[1,2-a]pyrazol-1-one type.

Suitable pyridine derivatives include, but are not limited to, the compounds described, for example, in British Patent Nos. 1 026 978 and 1 153 196, as well as 2,5-diaminopyridine, 2-(4-methoxyphenyl)amino-3-aminopyridine, 2,3-diamino-6-methoxy-pyridine, 2-(β-methoxyethyl)amino-3-amino-6-methoxypyridine, 3,4-diaminopyridine, and the acid addition salts thereof.

Non-limiting examples of pyrimidine derivatives include the compounds described, for example, in German Patent No. 2 359 399; Japanese Patent Application No. 88-169 571; Japanese Patent No. 05-163124; European Patent No. 0 770 375, and International Patent Application Publication No. WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethyl-pyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolyl-propylaminopyrazolo[1,5-a]pyrimidine, the acid addition salts thereof, and the tautomeric forms thereof, when a tautomeric equilibrium exists.

The pyrazole derivatives may be chosen, for example, from the compounds described in German Patent Nos. 3 843 892 and 4 133 957, German Patent Application No. 195 43 988, International Patent Application Nos. WO 94/08969 and WO 94/08970, and French Patent Application No. 2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(P-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methyl-aminopyrazole, 3,5-diamino-4-(β-hydroxyethyl)amino-1-methylpyrazole, and the acid addition salts thereof.

Examples of derivatives of pyrazolo[1,2-a]pyrazol-1-one type include, but are not limited to, compounds such as 2,3-diamino-6,7-dihydro-1H,5H-pyrazolo[1,2-a]pyrazole-1-one.

When present, the at least one oxidation base is present in the dye composition of the present disclosure in an amount ranging from 0.001% to 10% by weight relative to the total weight of the dye composition, for example, from 0.005% to 6% by weight relative to the total weight of the dye composition.

Couplers

The composition of the present disclosure may also comprise at least one coupler conventionally used for dyeing human keratin fibers.

The at least one coupler may be chosen, for instance, from meta-phenylenediamines, meta-aminophenols, meta-diphenols, naphthalene-based couplers, and heterocyclic couplers.

Non-limiting examples of suitable couplers include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxy-ethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxy-benzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

When present, the at least one coupler is present in the dye composition of the present disclosure in an amount ranging from 0.001% to 10% by weight relative to the total weight of the dye composition, for example, from 0.005% to 6% by weight relative to the total weight of the dye composition.

In at least one embodiment, the acid addition salts that may be used for the oxidation bases and couplers may be chosen from hydrochlorides, hydrobromides, sulfates, citrates, succinates, tartrates, lactates, tosylates, benzenesulfonates, phosphates, and acetates.

Dyeing Medium

The dye composition of the present disclosure comprises a medium that is suitable for dyeing, also known as a dye support. The dyeing medium may be chosen from water and mixtures of water and at least one organic solvent to dissolve the compounds that are not sufficiently water-soluble.

The at least one organic solvent may be chosen, for example, from linear or branched monoalcohols or diols comprising from 2 to 10 carbon atoms, which, in at least one embodiment, are saturated, such as ethyl alcohol; isopropyl alcohol; hexylene glycol (2-methyl-2,4-pentanediol); neopentyl glycol; 3-methyl-1,5-pentanediol; aromatic alcohols such as benzyl alcohol and phenylethyl alcohol; glycols and glycol ethers, for instance, ethylene glycol monomethyl, monoethyl and monobutyl ether; propylene glycol and its ethers, for instance, propylene glycol monomethyl ether, butylene glycol, and dipropylene glycol; and diethylene glycol alkyl ethers, wherein the alkyl group is chosen, for example, from $C_1$-$C_4$ alkyls, for instance, diethylene glycol monoethyl ether and diethylene glycol monobutyl ether, and mixtures thereof.

When present, the at least one solvent is present in the dye composition in an amount ranging from 1% to 40% by weight, for example, from 5% to 30% by weight relative to the total weight of the dye composition.

Adjuvants

The dye composition may also contain at least one adjuvant conventionally used in compositions for dyeing the hair, such as anionic, cationic, nonionic, amphoteric, and zwitterionic polymers and mixtures thereof other than the thickening polymers mentioned previously; antioxidants; penetrants; sequestrants; fragrances; buffers; dispersants; conditioning agents, for instance, silicones, which may or may not be volatile or modified; film-forming agents; ceramides; preserving agents; and opacifiers.

The at least one adjuvant may be present in the dye composition in an amount, for each of them, ranging from 0.01% to 20% by weight relative to the total weight of the dye composition.

The pH of the dye composition may range, for example, from 3 to 12, for instance, from 5 to 11. The pH may be adjusted to the desired value using acidifying or basifying agents conventionally used in the dyeing of keratin fibers, or alternatively, using standard buffer systems.

The acidifying agents may be chosen, for example, from mineral or organic acids such as hydrochloric acid, orthophosphoric acid, sulfuric acid, carboxylic acids such as acetic acid, tartaric acid, citric acid, and lactic acid, and sulfonic acids.

The basifying agents may be chosen, for example, from aqueous ammonia, alkaline carbonates, alkanolamines such as monoethanolamine, diethanolamine, and triethanolamine and derivatives thereof, sodium hydroxide, potassium hydroxide, and compounds having the following formula:

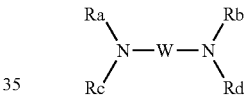

wherein W is a propylene residue optionally substituted with a hydroxyl group or a $C_1$-$C_4$ alkyl radical; and $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The dye composition according to the present disclosure may be in various forms, such as liquids, creams, and gels, or in any other form that is suitable for dyeing human keratin fibers.

Oxidizing Agent

The composition of the present disclosure may also comprise at least one oxidizing agent.

Usually, a ready-to-use composition may be obtained by mixing a dye composition comprising at least one compound of formula (I) free of oxidizing agent with an oxidizing composition.

It is also possible to simultaneously or successively apply a composition comprising at least one compound of formula (I) free of oxidizing agent, and a composition comprising at least one oxidizing agent.

The at least one oxidizing agent may be chosen from oxidizing agents conventionally used in the field, for example, hydrogen peroxide, urea peroxide, alkali metal bromates, persalts such as perborates and persulfates, and enzymes, for example, peroxidases, 2-electron oxidoreductases such as uricases, and 4-electron oxygenases, for instance, laccases.

In at least one embodiment, the at least one oxidizing agent is hydrogen peroxide.

The at least one oxidizing agent is present in the ready-to-use composition in an amount ranging from 1% to 40% by weight relative to the total weight of the ready-to-use composition, for example, from 1% to 20% by weight relative to the total weight of the ready-to-use composition.

The composition that is finally applied to the keratin fibers may be in various forms, such as liquids, creams, and gels, or in any other form that is suitable for dyeing human keratin fibers.

Dyeing Process

The process of the present disclosure may be performed on dry or wet fibers.

According to a first embodiment, the direct dyeing process comprises the application of a dye composition comprising at least one dye of formula (I) to human keratin fibers, in the absence of oxidizing agents, oxidation bases, and couplers. After a sufficient leave-on time, the fibers are optionally rinsed, to reveal dyed fibers.

According to a second embodiment, a dye composition comprising at least one dye of formula (I) is applied to human keratin fibers in the presence of at least one oxidizing agent, but in the absence of oxidation bases and couplers, which causes bleaching of the fiber (lightening direct dyeing). As indicated previously, the at least one oxidizing agent may be added to the composition comprising the at least one direct dye of formula (I) just before the application or may be applied directly to the fiber.

Also disclosed herein is an oxidation dyeing process in which a dye composition comprising at least one dye of formula (I), at least one oxidation base, and optionally at least one coupler is applied to wet or dry human keratin fibers, in the presence of an oxidizing agent.

In the context of oxidation dyeing or lightening direct dyeing, the dye composition is mixed with a composition containing, in a medium that is suitable for dyeing, at least one oxidizing agent, this oxidizing agent being present in an amount that is sufficient to develop a coloration. In at least one embodiment, the dye composition and the oxidizing composition are mixed at the time of use. The mixture obtained is then applied to the fibers.

In the dyeing processes of the present disclosure, regardless of the variant used (i.e., with or without oxidizing agent), the leave-on time generally ranges from 3 to 50 minutes, for example, from 5 to 30 minutes.

The process of the present disclosure may further comprise additional steps such as rinsing the fibers, washing with shampoo, drying, etc.

Multi-Compartment Device

Further disclosed herein is a multi-compartment device, or "kit", for dyeing human keratin fibers, for instance, the hair, comprising at least one first compartment containing a dye composition of the present disclosure free of oxidizing agent and at least one second compartment containing an oxidizing composition.

This device may be equipped with a means for applying the desired mixture to the hair, such as the devices described in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLE

The compositions below were prepared and used to dye human hair in red shades.

| | |
|---|---|
| Dye A or B | 0.5 g |
| Hydroxyethylcellulose (NATROSOL 250 HHR from Aqualon) | 1.0 g |
| Ethanol | 5 g |
| 2-Amino-2-methyl-1-propanol | qs pH 8 |
| Water | qs 100 g |

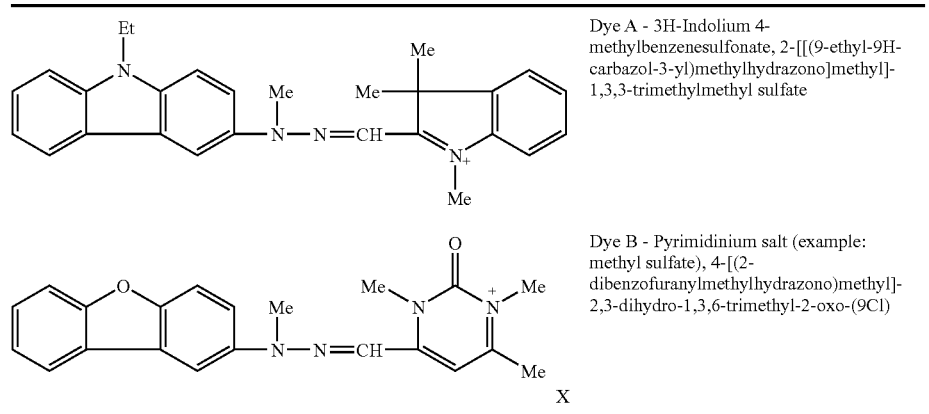

Dye A - 3H-Indolium 4-methylbenzenesulfonate, 2-[[(9-ethyl-9H-carbazol-3-yl)methylhydrazono]methyl]-1,3,3-trimethylmethyl sulfate Dye B - Pyrimidinium salt (example: methyl sulfate), 4-[(2-dibenzofuranylmethylhydrazono)methyl]-2,3-dihydro-1,3,6-trimethyl-2-oxo-(9Cl)

X

What is claimed is:

1. A dye composition comprising, in a medium suitable for dyeing human keratin fibers:

(a) at least one direct dye chosen from cationic direct hydrazone dyes of formula (I) and tautomeric forms thereof:

$$[A-C(R_3)=N-N(R_1)-B]^+X \qquad (I)$$

wherein:

$R_1$ and $R_3$, which may be identical or different, are chosen from hydrogen and linear or branched $C_1$-$C_{10}$ alkyl radicals optionally bearing a hydroxyl group;

A is a fused or non-fused, optionally substituted cationic heterocycle chosen from pyrimidinone, indole, and benzothiazole rings; the ring A being linked to the carbon of $C(R_3)$ via a carbon atom;

B is a saturated or unsaturated, optionally substituted tricycle chosen from dibenzofurans, carbazoles, anthraquinones, and dibenzothienyls; the saturated or unsaturated tricycle B being linked to the nitrogen atom of the hydrazone function via a carbon atom of one of the three rings;

X is chosen from anions and mixtures of anions that are cosmetically acceptable;

(b) at least one cosmetic agent chosen from thickening polymers and surfactants.

2. The composition of claim 1, wherein $R_1$ and $R_3$, which may be identical or different, are chosen from hydrogen and linear or branched $C_1$-$C_{10}$ alkyl radicals.

3. The composition of claim 1, wherein the group A of formula (I) is chosen such that one of the tautomeric forms has a quaternized nitrogen atom engaged in the heterocycle; said nitrogen atom bearing a substituent chosen from linear or branched $C_1$-$C_{10}$ alkyl radicals; linear or branched $C_1$-$C_{10}$ hydroxyalkyl radicals; benzyl and phenyl radicals optionally substituted on the aromatic ring, the aromatic nucleus of the benzyl and phenyl groups possibly being substituted with at least one radical chosen from $C_1$-$C_4$ alkyl radicals, $C_1$-$C_4$ alkoxy radicals, $C_1$-$C_4$ hydroxyalkyl radicals, amino radicals, and halogen radicals.

4. The composition of claim 1, wherein the group A of formula (I) is chosen such that:

the heterocycle or the heterocyclic portion of the group A is optionally substituted with at least one radical chosen from linear or branched $C_1$-$C_6$ alkyl radicals, hydroxyl radicals, amino radicals, $C_1$-$C_4$ alkoxy radicals, and halogen radicals, and the aromatic portion of the group A is optionally substituted with at least one radical chosen from trifluoromethyl radicals; ($C_1$-$C_6$)alkoxycarbonyl radicals; nitro radicals, hydroxyl radicals, $C_1$-$C_4$ alkyl radicals, $C_1$-$C_4$ alkoxy radicals, amino radicals, and halogen radicals.

5. The composition of claim 4, wherein the heterocycle of the heterocyclic portion of the group A is optionally substituted with at least one radical chosen from linear or branched $C_1$-$C_4$ alkyl radicals.

6. The composition of claim 1, wherein the group B is optionally substituted with at least one radical chosen from linear or branched $C_1$-$C_6$ alkyl radicals; linear or branched $C_1$-$C_6$ alkoxy radicals; amino radicals; amino radicals substituted with one or two linear or branched $C_1$-$C_6$ alkyl radicals, which may be identical or different; phenylamino radicals for which the phenyl group is optionally substituted; hydroxyl groups; halogen atoms; and nitro groups.

7. The composition of claim 1, wherein if the group B is an anthraquinone group, then this group may be substituted, with a group of formula

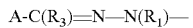
$$A-C(R_3)=N-N(R_1)-$$

wherein A, $R_1$, and $R_3$ are as defined in claim 1 and are chosen such that they are, respectively, identical to those of the other portion of the molecule of formula (I).

8. The composition of claim 7, wherein the group B is an anthraquinone group substituted on the other aromatic nucleus with the group of formula:

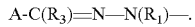
$$A-C(R_3)=N-N(R_1)-.$$

9. The composition of claim 1, wherein if the group B is an anthraquinone group, the radical $R_1$ is hydrogen.

10. The composition of claim 1, wherein X is chosen from halides; hydroxides; sulfates; hydrogen sulfates; ($C_1$-$C_6$) alkyl sulfates; phosphates; carbonates; hydrogen carbonates; perchlorates; acetates; tartrates; citrates, oxalates; ($C_1$-$C_6$) alkylsulfonates; arylsulfonates optionally substituted with a $C_1$-$C_4$ alkyl radical; and trichlorozincates.

11. The composition of claim 1, wherein the at least one direct dye is present in the composition in an amount ranging from 0.001% to 5% by weight relative to the total weight of the dye composition.

12. The composition of claim 11, wherein the at least one direct dye is present in the dye composition in an amount ranging from 0.05% to 2% by weight relative to the total weight of the dye composition.

13. The composition of claim 1, wherein the at least one thickener is chosen from:

(i) associative thickeners;
(ii) crosslinked acrylic acid homopolymers;
(iii) crosslinked copolymers of (meth)acrylic acid and of ($C_1$-$C_6$)alkyl acrylate;
(iv) nonionic homopolymers and copolymers containing ethylenically unsaturated monomers of ester and/or amide type;
(v) ammonium acrylate homopolymers or copolymers of ammonium acrylate and of acrylamide;
(vi) polysaccharides;
(vii) $C_{12}$-$C_{30}$ fatty alcohols;
(viii) mineral thickeners; and
mixtures thereof.

14. The composition of claim 13, wherein the at least one thickener is a polymeric organic thickener.

15. The composition of claim 1, wherein the at least one thickener is present in the dye composition in an amount ranging from 0.001% to 20% by weight relative to the total weight of the dye composition.

16. The composition of claim 1, wherein the at least one thickener is present in the dye composition in an amount ranging from 0.01% to 10% by weight relative to the total weight of the dye composition.

17. The composition of claim 1, wherein the at least one thickener is present in the dye composition in an amount ranging from 0.1% to 3% by weight relative to the total weight of the dye composition.

18. The composition of claim 1, wherein the at least one surfactant is chosen from anionic surfactants, amphoteric surfactants, cationic surfactants, and mixtures thereof.

19. The composition of claim 18, wherein the at least one surfactant is present in the dye composition in an amount ranging from 0.1% to 60% by weight relative to the total weight of the dye composition.

20. The composition of claim 19, wherein the at least one surfactant is present in the dye composition in an amount ranging from 5% to 30% by weight relative to the total weight of the dye composition.

21. The composition of claim 1, further comprising at least one additional direct dye other than the dye of formula (I), chosen from nitro dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, natural dyes, and mixtures thereof.

22. The composition of claim 1, further comprising at least one oxidation base chosen from o-phenylenediamines, p-phenylenediamines, double bases, o-aminophenols, p-aminophenols, heterocyclic bases, acid addition salts thereof, and mixtures thereof, and optionally comprising a coupler chosen from m-aminophenols, m-phenylenediamine, m-diphenols, naphthols, heterocyclic couplers, acid addition salts thereof, and mixtures thereof.

23. The composition of claim 1, further comprising at least one oxidizing agent.

24. A process for dyeing human keratin fibers comprising applying a dye composition to the fibers, wherein the dye composition comprises, in a medium suitable for dyeing human keratin fibers:

(a) at least one direct dye chosen from cationic direct hydrazone dyes of formula (I) and the tautomeric forms thereof:

$$[A-C(R_3)=N-N(R_1)-B]^+X \qquad (I)$$

wherein:
R$_1$ and R$_3$, which may be identical or different, are chosen from hydrogen and linear or branched C$_1$-C$_{10}$ alkyl radicals optionally bearing a hydroxyl group;

A is a fused or non-fused, optionally substituted cationic heterocycle chosen from pyrimidinone, indole, and benzothiazole rings; the ring A being linked to the carbon of C(R$_3$) via a carbon atom;

B is a saturated or unsaturated, optionally substituted tricycle chosen from dibenzofurans, carbazoles, anthraquinones, and dibenzothienyls; the saturated or unsaturated tricycle B being linked to the nitrogen atom of the hydrazone function via a carbon atom of one of the three rings;

X is chosen from anions and mixtures of anions that are cosmetically acceptable; and (b) at least one cosmetic agent chosen from thickening polymers and surfactants.

25. A multi-compartment device comprising at least one first compartment containing a dye composition and at least one second compartment containing an oxidizing composition, wherein the dye composition comprises, in a medium suitable for dyeing human keratin fibers:

(a) at least one direct dye chosen from cationic direct hydrazone dyes of formula (I) and the tautomeric forms thereof:

$$[A-C(R_3)=N-N(R_1)-B]^+X \qquad (I)$$

wherein:
R$_1$ and R$_3$, which may be identical or different, are chosen from hydrogen and linear or branched C$_1$-C$_{10}$ alkyl radicals optionally bearing a hydroxyl group;

A is a fused or non-fused, optionally substituted cationic heterocycle chosen from pyrimidinone, indole, and benzothiazole rings; the ring A being linked to the carbon of C(R$_3$) via a carbon atom;

B is a saturated or unsaturated, optionally substituted tricycle chosen from dibenzofurans, carbazoles, anthraquinones, and dibenzothienyls; the saturated or unsaturated tricycle B being linked to the nitrogen atom of the hydrazone function via a carbon atom of one of the three rings;

X is chosen from anions and mixtures of anions that are cosmetically acceptable; and (b) at least one cosmetic agent chosen from thickening polymers and surfactants.

* * * * *